(12) United States Patent
Raichart

(10) Patent No.: US 10,449,744 B1
(45) Date of Patent: Oct. 22, 2019

(54) CONTINUOUS ROSIN ROLLER PRESS AND RELATED METHODOLOGIES

(71) Applicant: Cullen Raichart, San Diego, CA (US)

(72) Inventor: Cullen Raichart, San Diego, CA (US)

( * ) Notice: Subject to any disclaimer, the term of this patent is extended or adjusted under 35 U.S.C. 154(b) by 0 days.

(21) Appl. No.: 15/994,038

(22) Filed: May 31, 2018

(51) Int. Cl.
| | |
|---|---|
| *B30B 9/12* | (2006.01) |
| *B30B 9/20* | (2006.01) |
| *B30B 9/26* | (2006.01) |
| *A23D 7/005* | (2006.01) |
| *B30B 15/30* | (2006.01) |
| *B30B 15/34* | (2006.01) |

(52) U.S. Cl.
CPC .............. *B30B 9/265* (2013.01); *B30B 9/127* (2013.01); *B30B 9/20* (2013.01); *B30B 15/308* (2013.01); *B30B 15/34* (2013.01); *A23D 7/005* (2013.01); *A61K 2236/31* (2013.01); *A61K 2236/37* (2013.01); *A61K 2236/53* (2013.01)

(58) Field of Classification Search
CPC .. B30B 9/20; B30B 9/24; B30B 9/241; B30B 9/245; B30B 9/246; B30B 9/265; B30B 15/308; A61K 2236/31; A61K 2236/37; A61K 2236/53
See application file for complete search history.

(56) References Cited

U.S. PATENT DOCUMENTS

| | | | |
|---|---|---|---|
| 2004/0118418 A1* | 6/2004 | Hancock | A24C 5/00 131/65 |
| 2017/0239304 A1* | 8/2017 | Pence | A23D 7/005 |

FOREIGN PATENT DOCUMENTS

| | | | | |
|---|---|---|---|---|
| GB | 201190 A | * | 7/1923 | B30B 9/24 |

\* cited by examiner

*Primary Examiner* — Gregory D Swiatocha
(74) *Attorney, Agent, or Firm* — Buche & Associates, P.C.; John K. Buche; Bryce A. Johnson

(57) ABSTRACT

In general, the roller press provides plant products into a canal of a ribbon stream, encapsulates the plant products via the ribbon, and presses rosin from the encapsulated products so that waste products and the ribbon are discarded while the rosin is collected from of the surfaces of the press.

1 Claim, 1 Drawing Sheet

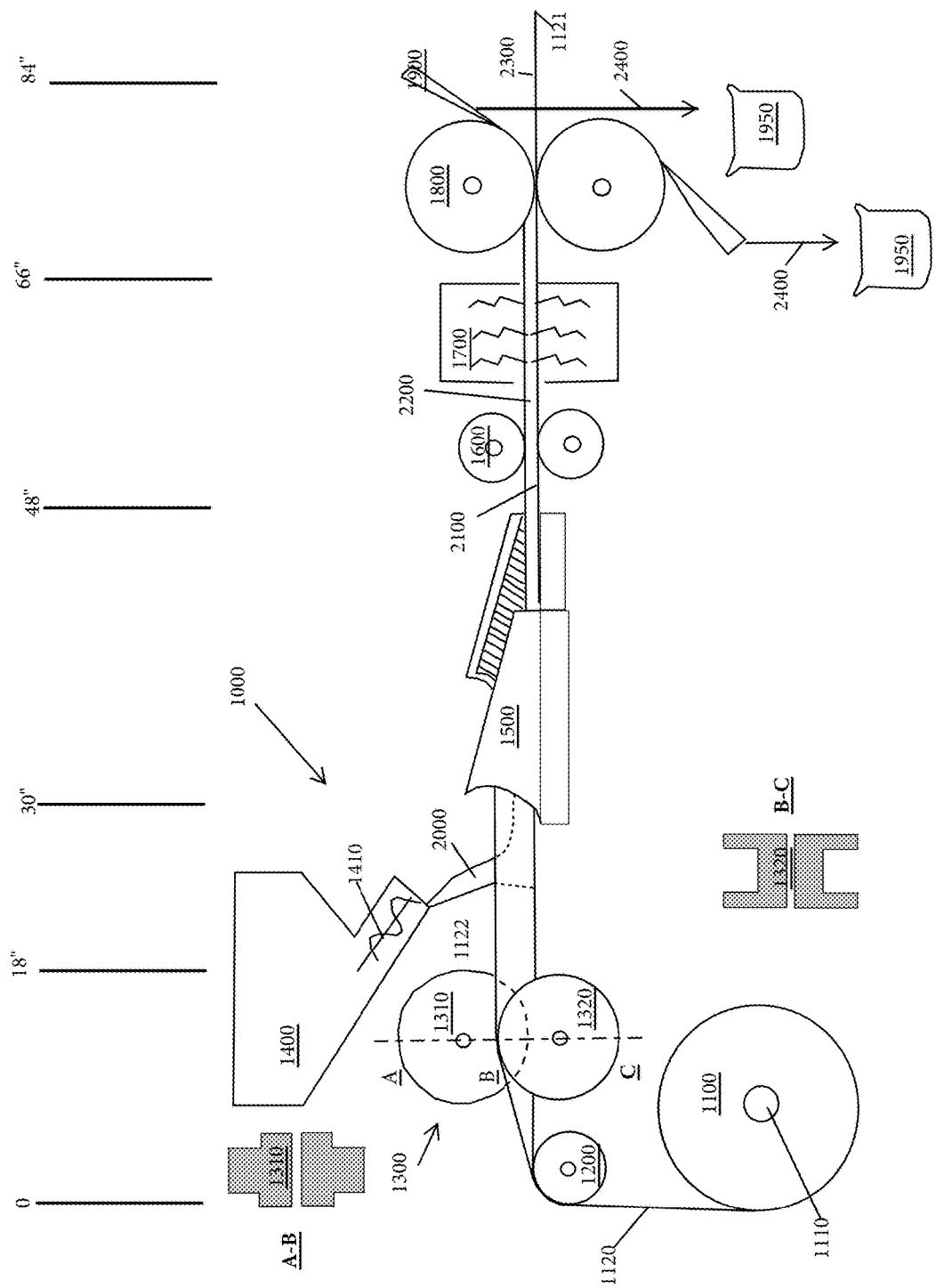

CONTINUOUS ROSIN ROLLER PRESS AND RELATED METHODOLOGIES

CROSS-REFERENCE TO RELATED APPLICATIONS

Not applicable.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO AN APPENDIX SUBMITTED ON A COMPACT DISC AND INCORPORATED BY REFERENCE OF THE MATERIAL ON THE COMPACT DISC

Not applicable.

STATEMENT REGARDING PRIOR DISCLOSURES BY THE INVENTOR OR A JOINT INVENTOR

Reserved for a later date, if necessary.

BACKGROUND OF THE INVENTION

Field of Invention

The disclosed subject matter is in the field of roller presses and, in particular, rosin roller presses.

Background of the Invention

Plants and other objects can contain essential oils and resins (sap) that can be applied to recreational, medicinal, therapeutic and cosmetic applications. In particular, recreational and medicinal cannabis use by the public at large has substantially increased in recent years due to legalization of such activities in several States. So, it comes as no surprise that various processes have been developed for extracting resins and essential oils from plants.

In modern times, toxic solvents (including light hydrocarbons like butane or propane) have been used to chemically extract resins and oils from plants or similar objects. However, because the solvents are toxic, the extracted resin must be purified before it can be used. Problems arise at this point in a process because purification involves a complicated separation process. Accordingly, a need exits for non-chemical extraction techniques and processes for removing resins and oils from plants.

In view of this need, flat rosin presses have been developed for extracting plant resin/oil. Presses that combine heat and pressure to extract resin or oil from plants are known. Such flat rosin presses involve applying downward or horizontal pressure to gathered-plants on a hot plate so that resin is released. These presses are, indeed, preferred by many users since presses are mechanical as opposed to solvent-based extraction of resin or oils.

But, even while preferred, these flat presses are not satisfactory for mass production of rosin. Once the resin is released, the plant pulp must be separated from the resin so that the resin can be gathered up from the hot plate. Separating the pulp and removing the resin from the hotplate is often tedious and time consuming. Also, such rosin presses cannot process a large amount of resin at once because pressure from the hydraulic piston can cause too much resin to spew out the sides of the hotplate. Thus, a need exists for improved resin presses and related methodologies that are adapted to mass production and that do not entail the drawbacks associated with known resin presses.

SUMMARY OF THE INVENTION

In view of the foregoing, an object of this specification is to disclose a continuous rosin roller press and related methodologies. It is further an objective to disclose a rosin roller press, system, and process for mass production of rosin from cannabis or other plant material.

In a typical embodiment, the roller press comprises:
- a roll good (e.g., fabric rolled up on a core) or reel of cloth or mesh material placed on a spindle or other mechanism that enables the roll of cloth or mesh material to be unrolled into a ribbon when the fabric is drawn out by its free end;
- an idle roller for guiding and spreading drawn out cloth or mesh from the roll good;
- a roll former for rollforming the ribbon of cloth or mesh into a single stage canal by upturning the lengthwise edges of the ribbon;
- a surge hopper with a screw feeder for dispending cannabis or other plant product;
- a fold guide for overturning the upturned edges of the ribbon to create a tubiform within which is located the cannabis or other plant product deposited into the canal by the hopper;
- compression rollers for flattening the cannabis or other plant product within the tubiform ribbon;
- a preheater for increasing the temperature of the cannabis or other plant product within the flattened tubiform ribbon;
- thermal rollers for pressing the flattened and preheated cannabis or other plant product within the flattened tubiform ribbon;
- scrapers for scraping resin emitted from the pressed tubiform ribbon off of the thermal rollers; and,
- rosin catch containers for collecting rosin from the scrapers.

In a preferred system, the roll good or reel is positioned so that the free end of the fabric may be provided over the idle roller, through the roll former, under the surge hopper to receive product, through the fold guides, through the compression roller, through the preheater, through the thermal roller where resin is pressed from the product and is collected on the surface of the thermal rollers, and discarded. Resin may be scraped from the thermal rollers and collected in containers.

In one suitable practice, a mesh material may be fed onto the belt from a spool. The mesh material proceeds through a roll former (including a female roll former and cooperating male roll former) to create a mesh profile to catch the product from the surge hopper. Suitably, the product is metered from the surge hopper to ensure consistent volume is dispensed into the mesh. The mesh-product combination travels first through guides that fold the mesh onto itself to encapsulate the product. The subsequent encapsulated product then travels through a compression roller to flatten the mesh-product combination. Next, the combination is passed through a pre-heat stage, elevating the product temperature, and then through compression thermal rollers that suitably induce a change to both the physical and chemical properties of the product while the mesh separates rosin from undesired materials. Finally, the rosin is then removed from the rollers via a combination of scrapers and collected in containers for further processing and packaging.

BRIEF DESCRIPTION OF THE SEVERAL VIEWS OF THE DRAWINGS

Other objectives of the disclosure will become apparent to those skilled in the art once the invention has been shown and described. The manner in which these objectives and other desirable characteristics can be obtained is explained in the following description and attached figures in which:

FIG. 1 is a process flow diagram for the continuous rosin roller press and related methodologies.

1000—Roller press assembly
1100—a reel of cloth or mesh material;
1110—spindle
1120—ribbon of cloth or mesh
1121—free end;
1122—upturned edges
1200—idle roller for guiding and spreading the ribbon;
1300—roll former;
1310—male roll former;
1320—female roll former;
1400—surge hopper
1410—screw feeder;
1500—fold guide;
1600—compression rollers;
1700—preheater;
1800—thermal rollers;
1900—scrapers;
1950—rosin catch containers.
2000—cannabis or other plant product;
2100—encapsulated product;
2200—flattened product;
2300—waste product; and,
2400—rosin.

It is to be noted, however, that the appended figures illustrate only typical embodiments of this invention and are therefore not to be considered limiting of its scope, for the invention may admit to other equally effective embodiments that will be appreciated by those reasonably skilled in the relevant arts. Also, figures are not necessarily made to scale but are representative.

DETAILED DESCRIPTION OF PREFERRED EMBODIMENTS

Disclosed is a continuous rosin roller press and related methodologies. In general, the roller press provides plant products into a canal of a ribbon stream, encapsulates the plant products via the ribbon, and presses rosin from the encapsulated products so that waste products and the ribbon are discarded while the rosin is collected from of the surfaces of the press. The more detailed description of the preferred embodiments are provided below in connection with the figures.

FIG. 1 is a process flow diagram of the disclosed system and roller press assembly 1000. As shown, the roller press assembly 1000 comprises the reel 1100 of cloth or mesh material placed on a spindle 1110 or other mechanism that enables the roll 1100 of cloth or mesh material to be unrolled into a ribbon 1120 when drawn out by its free end 1121; an idle roller 1200 for guiding and spreading the ribbon 1120; a roll former (1300) (including male and female roll formers 1310, 1320) for rollforming the ribbon 1120 into a single stage canal by upturning the lengthwise edges 1122 of the ribbon 1120; a surge hopper 1400 with a screw feeder 1410 for dispending cannabis or other plant product 2000; a fold guide 1500 for overturning the upturned edges 1122 of the ribbon 1120 to create a tubiform within which is encapsulated the cannabis or other plant product (encapsulated product 2100) (e.g., product 2000 that was deposited into the ribbon's 1120 canal by the hopper 1400); compression rollers 1600 for flattening the cannabis or other plant product (flattened product 2200); a preheater 1700 for increasing the temperature of the flattened product 2200; thermal rollers 1800 for pressing the flattened and preheated cannabis or other plant product 2200 to product rosin 2400 on the surface of the rollers 1800 and a waste product 2300; scrapers 1900 for scraping rosin 2400 emitted from the pressed tubiform ribbon 2200 off of the thermal rollers 1800; and, rosin catch containers 150 for collecting rosin 2400 from the scrapers 1900.

FIG. 1 further shows the material reel 1100 where the material reel 1100 unspools a mesh material 1120 towards the idle roller 1200. Suitably, the idle roller 1200 reorients the mesh material 1100 and propels it towards the female roll former 1320 and male roll former 1310 so that the surface of the mesh material runs between the contact point of the male roll former 1310 and the female roll former 1320.

FIG. 1 also shows the female roll former 1320 which exhibits a U-shaped indent, and the male roll former 1310 exhibits a stout central protrusion (cross-sections A-B and B-C respectively depicted in FIG. 1) for cooperating with the female roll former's 1320 U-shape. The male roll former 1310 is transposed to the female roll former 1320 and is fixated superiorly to the female roll former 1320 so that the complementary shapes of the roll formers meet together causing the superior ends if the U-shaped female roll former 1320 to meet the inferior ends of the cross portion of the male roll former 1310. Suitably, the material reel 1100, the idle roller 1200, and the roll formers 1300 are within about 18 inches of each other.

Still referring to FIG. 1, the mesh material 1120 may be propelled between the transposed roll formers 1300. The male form roller 1310 suitably pushes downward on the mesh material 1120 and forces the material into the U-shaped crevice of the female roll former 1320. The mesh material 1120 may suitably conform to the U-shape of the female roll former 1320 to create a canal via upturned edges 1122.

Yet still referring to FIG. 1, the surge hopper 1400, fixated at about 18 inches from the roll former and above the ribbon 1120 of the roller assembly 1000, preferably collects and retains a plant material 2000 in the ribbon 1120 with upturned sides 1122. The mesh material is deposited from the surge bin 1400 onto the female belt 1100 via the screw feeder 1410. The now U-shaped mesh material 1120 collects and prevents escape of the plant material 2000. The mesh material 1120, holding the deposited plant material 2000, may typically travel through the fold guides 1500 (after about 12 inches for catching the product 2000) which fold the lateral sides 1122 of the U-shaped mesh material 1120 so that they meet, encapsulating the plant material (2100).

The compression rollers 1600 are transposed and oppositionally fixated on either side of the roller assembly 1000. The compression rollers 1600 suitably provide pressure to the mesh material 1120 enveloping the plant material, compressing the encapsulated material 2100. Suitably, the flat encapsulated material 2200 is propelled through a preheater 1700 that heats the product compressed between the mesh material 1120 to a desired temperature.

The flat and preheated material 2200 may suitably be drawn through thermal rollers 1800. The thermal rollers 1800 are oppositionally fixated to the roller assembly 1000 to provide heat and pressure to the flat and encapsulated product 2200 through compression. The compression provided at this contact point of the thermal rollers 1800 preferably induces both a chemical and physical change in the product within the ribbon 2200 resulting in a leakage of rosin 2400 through the mesh material 2200 onto the surface of the rollers 1800. The extracted rosin 2400 adheres to the thermal rollers 1800 and is removed from the roll formers by scrapers 1900 as the thermal rollers 1800 continue to spin. The scrapers 1900 are suitably positioned against the thermal rollers 1800 to remove the extracted rosin 2400 via scraping as the thermal rollers 1800 continue to spin and collect rosin 2400. As shown, the rosin 2400 collected from the thermal rollers 1800 via the scrapers 1900 accumulates on the scrapers 1900 and typically the force of gravity pulls at the rosin 2400 causing it to drip off the scraper 1900 and collect in an inferiorly positioned rosin collection container 1950. The length of the assembly 1000 is preferably about 84 inches.

In a preferred system, the roll good or reel is positioned so that the free end of the fabric may be provided over the idle roller, through the roll former, under the surge hopper to receive product, through the fold guides, through the compression roller, through the preheater, through the thermal roller where resin is pressed from the product and is collected on the surface of the thermal rollers, and discarded. Resin may be scraped from the thermal rollers and collected in containers.

Although the method and apparatus is described above in terms of various exemplary embodiments and implementations, it should be understood that the various features, aspects and functionality described in one or more of the individual embodiments are not limited in their applicability to the particular embodiment with which they are described, but instead might be applied, alone or in various combinations, to one or more of the other embodiments of the disclosed method and apparatus, whether or not such embodiments are described and whether or not such features are presented as being a part of a described embodiment. Thus the breadth and scope of the claimed invention should not be limited by any of the above-described embodiments.

Terms and phrases used in this document, and variations thereof, unless otherwise expressly stated, should be construed as open-ended as opposed to limiting. As examples of the foregoing: the term "including" should be read as meaning "including, without limitation" or the like, the term "example" is used to provide exemplary instances of the item in discussion, not an exhaustive or limiting list thereof, the terms "a" or "an" should be read as meaning "at least one," "one or more," or the like, and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that might be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases might be absent. The use of the term "assembly" does not imply that the components or functionality described or claimed as part of the module are all configured in a common package. Indeed, any or all of the various components of a module, whether control logic or other components, might be combined in a single package or separately maintained and might further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives might be implemented without confinement to the illustrated examples. For example, block diagrams and their accompanying description should not be construed as mandating a particular architecture or configuration.

All original claims submitted with this specification are incorporated by reference in their entirety as if fully set forth herein.

I claim:

1. A method of extracting rosin from cannabis or other plant products, said method comprising the steps of:

obtaining a continuous roller press assembly comprising—
  a reel material that is drawn out to a ribbon,
  an idle roller for guiding and spreading the ribbon,
  a roll former for roll-forming the ribbon into a canal by upturning lengthwise edges of the ribbon,
  a surge hopper for dispensing the cannabis or other plant products, said surge hopper positioned over the ribbon and configured to deposit the cannabis or other plant products into the canal of the ribbon,
  fold guides for overturning the upturned lengthwise edges of the ribbon to encapsulate the cannabis or other plant products provided to the ribbon,
  compression rollers for flattening the cannabis or other plant products encapsulated by the ribbon,
  a preheater for increasing the temperature of the flattened cannabis or other plant products encapsulated by the ribbon;
  thermal rollers for pressing the flattened and preheated cannabis or other plant products encapsulated by the ribbon to produce the rosin on the surfaces of the thermal rollers and a waste product encapsulated by the ribbon,
  scrapers for scraping the rosin emitted from the pressed ribbon off of the thermal rollers, and,
  rosin catch containers for collecting the rosin from the scrapers;
stringing a free end of the ribbon over the idle roller, through the roll former, under the surge hopper, between the compression rollers, through the preheater, and between the thermal rollers; and,
providing the cannabis or other plant products to the hopper;
upturning the lengthwise edges of the ribbon via the roll former to create the canal in the ribbon;
depositing the cannabis or other plant products from the hopper into the canal;
overturning the upturned lengthwise edges of the ribbon via the fold guides to encapsulate the cannabis or other plant products in the canal of the ribbon;

flattening the encapsulated cannabis or other plant products via the compression rollers;
preheating the flattened cannabis or other plant products via the preheater;
pressing the rosin from the preheated cannabis or other plant products via the thermal rollers so that said rosin adheres to the surfaces of the thermal rollers;
scraping the rosin off of said surfaces of the thermal rollers via the scrapers;
collecting the rosin from the scrapers.

* * * * *